(12) United States Patent
Biffi

(10) Patent No.: US 11,400,124 B2
(45) Date of Patent: Aug. 2, 2022

(54) USE OF PROBIOTICS FOR IMPROVING PROTEIN ABSORPTION

(71) Applicant: SOFAR S.P.A., Trezzano Rosa (IT)

(72) Inventor: Andrea Biffi, Urgnano (IT)

(73) Assignee: SOFAR S.P.A., Trezzano Rosa (IT)

( * ) Notice: Subject to any disclaimer, the term of this patent is extended or adjusted under 35 U.S.C. 154(b) by 0 days.

(21) Appl. No.: 16/301,361

(22) PCT Filed: May 15, 2017

(86) PCT No.: PCT/IB2017/052850
§ 371 (c)(1),
(2) Date: Nov. 13, 2018

(87) PCT Pub. No.: WO2017/195182
PCT Pub. Date: Nov. 16, 2017

(65) Prior Publication Data
US 2019/0192590 A1    Jun. 27, 2019

Related U.S. Application Data

(60) Provisional application No. 62/335,926, filed on May 13, 2016.

(30) Foreign Application Priority Data

Aug. 8, 2016 (IT) .......................... 102016000083376

(51) Int. Cl.
| | | |
|---|---|---|
| *A61K 35/747* | (2015.01) |
| *A23L 33/135* | (2016.01) |
| *A61K 9/00* | (2006.01) |
| *A23L 33/17* | (2016.01) |
| *A23L 33/15* | (2016.01) |
| *A61P 1/00* | (2006.01) |
| *A23L 33/16* | (2016.01) |
| *A61K 35/741* | (2015.01) |
| *A23L 29/00* | (2016.01) |
| *A23L 29/238* | (2016.01) |
| *A23L 33/175* | (2016.01) |

(52) U.S. Cl.
CPC ............ *A61K 35/747* (2013.01); *A23L 29/06* (2016.08); *A23L 29/065* (2016.08); *A23L 29/238* (2016.08); *A23L 33/135* (2016.08); *A23L 33/15* (2016.08); *A23L 33/16* (2016.08); *A23L 33/17* (2016.08); *A23L 33/175* (2016.08); *A61K 9/0014* (2013.01); *A61K 9/0053* (2013.01); *A61K 35/741* (2013.01); *A61P 1/00* (2018.01)

(58) Field of Classification Search
None
See application file for complete search history.

(56) References Cited

U.S. PATENT DOCUMENTS

| | | |
|---|---|---|
| 5,531,989 A | 7/1996 | Paul |
| 6,770,246 B1 | 8/2004 | Husek |
| 7,510,734 B2 | 3/2009 | Sullivan et al. |
| 2002/0090416 A1 | 7/2002 | Connolly |
| 2003/0031659 A1* | 2/2003 | Farmer .................. A61K 31/43 424/93.45 |
| 2003/0092163 A1 | 5/2003 | Collins et al. |
| 2003/0157146 A1 | 8/2003 | Rautonen et al. |
| 2003/0190369 A1 | 10/2003 | Lovett |
| 2004/0170617 A1 | 9/2004 | Finegold |
| 2005/0196480 A1 | 9/2005 | Sullivan et al. |
| 2006/0057704 A1 | 3/2006 | Schlothauer et al. |
| 2006/0067921 A1 | 3/2006 | Conway |
| 2008/0081035 A1 | 4/2008 | Parmely et al. |
| 2008/0193603 A1 | 8/2008 | Hayes et al. |
| 2008/0241226 A1 | 10/2008 | Abeln et al. |
| 2009/0061446 A1 | 3/2009 | Niimi et al. |
| 2009/0098088 A1 | 4/2009 | Taylor et al. |
| 2009/0220481 A1 | 9/2009 | Maes et al. |
| 2009/0274662 A1 | 11/2009 | Magowan et al. |
| 2009/0312282 A1 | 12/2009 | Yoshida et al. |
| 2010/0074994 A1 | 3/2010 | Harel et al. |
| 2010/0112564 A1 | 5/2010 | Zhao et al. |
| 2011/0014167 A1 | 1/2011 | Bindels et al. |
| 2011/0038837 A1 | 2/2011 | Nishida et al. |
| 2011/0052538 A1 | 3/2011 | Brown et al. |
| 2011/0166100 A1 | 7/2011 | Wu |
| 2011/0305744 A1 | 12/2011 | Russo |
| 2012/0251512 A1 | 10/2012 | Farmer et al. |
| 2012/0269865 A1 | 10/2012 | Roughead et al. |
| 2012/0301451 A1 | 11/2012 | Braenning et al. |
| 2012/0322773 A1 | 12/2012 | Pravda |

(Continued)

FOREIGN PATENT DOCUMENTS

| | | |
|---|---|---|
| CN | 1161795 A | 10/1997 |
| CN | 1701116 A | 11/2005 |

(Continued)

OTHER PUBLICATIONS

Ferrario et al., J. Nutr. 144:1787-1796 (2014) (Year: 2014).*
Havea, Int. Dairy J., 16:415-422 (2006) (Year: 2006).*
Balzaretti et al., Front. Microbiol., 6(952):1-13 (2015) (Year: 2015).*
Ausubel et al, Current Protocols in molecular biology, edited vols. 1 and 2. John Wiley & Sons, Inc., Media, PA,1994.
Balzaretti et al., "A Novel rhamnose-rich heterp-exopolysaccharide isolated from Lactobacillus paracasei DG activates THP-1 human monocytic cells"*University of Huddersfiled Repository Article for Applied and Environmental Microbiology*.Jan. 17, 2017.
Balzaretti et al., "Exploring Lactobacillus paracasei probiosis and metabolic potential", University of Milan PhD thesis, 2015, pp. 1-132.

(Continued)

*Primary Examiner* — David W Berke-Schllessel
(74) *Attorney, Agent, or Firm* — Steinfl + Bruno LLP

(57) ABSTRACT

The present invention relates to the use of probiotics, preferably one or more probiotic bacteria, to increase the absorption of proteins or the bioavailability thereof, preferably in individuals with increased protein and/or energy requirements, preferably elderly persons, children, pregnant women or athletes.

9 Claims, No Drawings

(56) References Cited

U.S. PATENT DOCUMENTS

| | | | |
|---|---|---|---|
| 2016/0296569 A1 | 10/2016 | Guglielmetti et al. |
| 2016/0348155 A1 | 12/2016 | Guglielmetti et al. |
| 2017/0035816 A1 | 2/2017 | Biffi |
| 2019/0290706 A1 | 9/2019 | Biffi et al. |
| 2019/0345268 A1 | 11/2019 | Biffi et al. |
| 2021/0186075 A1 | 6/2021 | Biffi et al. |
| 2021/0236565 A1 | 8/2021 | Biffi |

FOREIGN PATENT DOCUMENTS

| | | | |
|---|---|---|---|
| CN | 1840206 A | 10/2006 |
| CN | 101636173 A | 1/2010 |
| EP | 1145643 A1 | 10/2001 |
| JP | H0517363 A | 1/1993 |
| JP | 2005508617 A | 4/2005 |
| JP | 2005534315 A | 11/2005 |
| JP | 2010512755 A | 4/2010 |
| JP | 2010161944 A | 7/2010 |
| JP | 2013515051 A | 5/2013 |
| RU | 2182008 C1 | 5/2002 |
| WO | 00/54788 A1 | 9/2000 |
| WO | 2003/090763 A1 | 11/2003 |
| WO | 2004/022727 A1 | 3/2004 |
| WO | 2005/001109 A2 | 1/2005 |
| WO | 2005/083122 A2 | 9/2005 |
| WO | 2006/050479 A2 | 5/2006 |
| WO | 2007/071815 A1 | 6/2007 |
| WO | 2008/119012 A2 | 10/2008 |
| WO | 2008/148798 A2 | 12/2008 |
| WO | 2010/008272 A1 | 1/2010 |
| WO | 2010/008278 A1 | 1/2010 |
| WO | 2011/036539 A1 | 3/2011 |
| WO | 2012/154738 A1 | 11/2012 |
| WO | 2014/068338 A1 | 5/2014 |
| WO | 2014/137211 A1 | 9/2014 |
| WO | 2015/000972 A1 | 1/2015 |
| WO | 2015/033304 A1 | 3/2015 |
| WO | 2015/033305 A1 | 3/2015 |
| WO | 2015/162570 A1 | 10/2015 |
| WO | 2017/195182 A1 | 11/2017 |
| WO | 2017/212433 A1 | 12/2017 |
| WO | 2018/100549 A1 | 6/2018 |
| WO | 2018/109730 A1 | 6/2018 |
| WO | 2021/090228 A1 | 5/2021 |

OTHER PUBLICATIONS

Ciucanu I. et al. "A simple and rapid method for the permethylation of carbohydrates" *Carbohydrate Research*,131(1984) pp. 209-217.
Collins M.N. and Birkinshaw C. "Hyaluronic acid based scaffolds for tissue engineering—A review", Carbohydrate Polymers 2013, 1262-1279.
Communication pursuant to Article 94(3) EPC for EP Application No. 14790322.3 filed on Sep. 5, 2014 on behalf of Sofar S.P.A.Mail Date: Jan. 31, 2020 8 pages.
Costalos et al., "Enteral feeding of premature infants with *Saccharomyces boulardii*" *Early Human Development*, 74,(2003), 89-96.
Crohn's and Colitis Foundation of America. Inflammatory Bowel Disease and Inflammatory Bowel Syndrome: Similarities and Differences.2014. 12 Pages.
De Souza M.M. et aJ. "Effects of budesonide and probiotics enemas on the systemic inflammatory response of rats with experimental coJitis", Acta Cirurgica Brasileira 2007, 22 (Supp 1. 1 ): 40-45.
Di Mario Francesco et al., "Use of mesalazine in diverticular disease." Journal of Clinical Gastroenterology. vol. 40, Suppl 3, Aug. 2006.
D'Inca R. et al. Rectal administration of Lactobacillus Casei DG modifies flora composition and Toll-Like receptor expression in colonic mucosa of patients with mildulcerative colitis'\ Dig. Dis. Sci. 2011, 56: 1178-1187.
EFSA Journal, "Scientific Opinion on the maintenance of the list of QPS biological agents intentionally added to food and feed (2012 update)1" EFSA Journal2012; 10(12):3020. 84 pages.
European Food Safety Authority EFSA journal (2012) 10(6): 2723.
Evans S. "Clinical trial structures"*J Exp Stroke Transl Med*.Mar. 2011, pp. 1-16, 16 pages .
"Example Cross-Over Study Design {A Phase 11, Randomized, Double-Blind Crossover Study of Hypertena and Placebo in Participants with High Blookd Pressure)". ClinicalTrials.gov (2012).
Fakhari A. and Berkland C. "Applications and emerging trends of hyaluronic acid in tissue engineering, as a dermal filler and in osteoarthritis treatment", Acta Biomaterialia2013, 9, 7081-7092.
Fao and Who et al; "Live microorganisms which, when administered in adequate amounts, confer a health benefit on the host", *World Health Organizations and Food Agriculture Organization*. 2001.
Farup et al., "Probiotics, Symptoms, and Gut Microbiota; What are the relations? A Randomized Controlled Trial in Subjects with Irritable Bowel Syndrome" Gastro Research and Practice, vol. 2012. 7 pages.
Final Office Action for U.S. Appl. No. 14/916,959, filed Mar. 4, 2016 on behalf of Sofar S.P.A.dated Aug. 21, 2020 48 pages.
Final Office Action for U.S. Appl. No. 14/916,959, filed Mar. 4, 2016 on behalf of Sofar Spa. dated Jul. 23, 2019. 23 pages.
Final Office Action for U.S. Appl. No. 14/916,961, filed Mar. 4, 2016 on behalf of Sofar S.P.Adated Jan. 2, 2020 16 pages.
Final Office Action for U.S. Appl. No. 14/916,961, filed Mar. 4, 2016 on behalf of Sofar S.P.A. dated Mar. 13, 2018. 15 pages.
Final Office Action for U.S. Appl. No. 15/305,470, filed Oct. 20, 2016 on behalf of Sofar Spa.dated Jan. 14, 2019. 10 pages.
Final Office Action for U.S. Appl. No. 14/916,959, filed Mar. 4, 2016 on behalf of Sofar Spa.dated Apr. 20, 2018. 26 pages.
Fiorino et al., "P325 Efficacy and Safety of IBD98E, a Sodium Hyaluronate Topical Preparation, in the Induction of Clinical and Endoscopic Remission in Patients with Distal Ulcerative Colitis: An Open Label Study," United European Gastroenterology Journal: 1(1S) (A219).
Floch M.H. et al. "Recommendations for probiotic use—2011 Update", J. CIin.Gastroenterol.2011, 45: S168-S171.
Food and Agriculture Organization. Health and nutritional properties of probiotics in food including powder milk with live lactic acid bacteria.Oct. 2001: 34 pages.
Gerwig G. et al., "Determination of the absolute configuration of mono-saccharides in complex carbohydrates by capillary G.L.C." *Carbohydrate Research*,77(1979) pp. 1-7.
Gill et al., "Metagenomic Analysis of the Human Distal Gut Microbiome," Science 312: 1355-1359 (2006).
Guglielmetti S. et al., "TgaA, a VirB1-Like Component Belonging to a Putative Type IV Secretion System of Bifidobacterium bifidum MIMBb75"*Applied and Environmental Microbiology*,vol. 80, No. 17,Sep. 2014 pp. 5161-5169.
Gugliemetti et al., "Randomised clinical trial; Bifidobacterium bifidum MIMBb75 significatnly alleviates irritable bowel syndrome and improves quality of life, a double-blind, placebo-controlled study" Alimentary Pharmacology & Therapeutics, p. 1123-1132. 2011.
Guo, Y., et al., "Irritable Bowel Syndrome is Positively Related to Metabolic Syndrome: A Population-Based Cross-Sectional Study," PLoS One. 9(11): e112289.Nov. 10, 2014. 6 pages.
International Search Report for International Application No. PCT/IB2014/064284 filed on Sep. 5, 2014 on behalf of Sofar SPA.dated Jan. 26, 2015. 6 pages.
International Search Report for International Application No. PCT/IB2014/064285 filed on Sep. 5, 2014 on behalf of Sofar SPA.dated Jan. 29, 2015. 4 pages.
International Search Report for International Application No. PCT/IB2017/052850 filed on May 15, 2017 on behalf of Sofar SPA.dated Aug. 17, 2017. 4 pages.
International Search Report for International Application No. PCT/IB2017/053389 filed on Jun. 8, 2017 on behalf of Sofar SPA.dated Oct. 6, 2017. 5 pages.
International Search Report for International Application No. PCT/IB2017/057576 filed on Dec. 1, 2017 on behalf of Sofar SPA.dated Feb. 22, 2018. 5 pages

(56) References Cited

OTHER PUBLICATIONS

International Search Report for International Application No. PCT/IB2017/057980 filed on Dec. 15, 2017 on behalf of Sofar SPA. dateD Mar. 19, 2018. 4 pages.
International Search report for International Application PCT/IB2015/052938 filed on Apr. 22, 2015 on behalf of Sofar SPA.dated Jul. 31, 2015. 4 pages.
Italia it Ministero della Salute (*Linee Guida su Probiotici e Prebiotici rev*.May 2013).
Jacobsen et al., "Screening of Probiotic Activities of Forty-Seven Strains of *Lactobacillus* spp. By in Vitro techniques and Evaluation of the Colonization Ability of Five Selected Strains in Humans" Applied and Environmental Microbiology, Nov. 1999, p. 4949-4956. 8 pages.
Larsen et al., "Predominant genera of fecal microbiota in children with atopic dermatitis are not altered by intake of probiolic bacteria *Lactobacillus acidophilus* NCFM and *Bifidobacterium animalis* subsp. *lacis* Bi-07," FEMS Microbiol Ecol 75: 482-496 (2011).
Laws et al., "Biosynthesis, characterization, and design of bacterial exopolysacharides from lactic acid bacteria",*Biotechnology Advances*. vol. 19,2001. pp. 597-625.
LeBlanc et al., "Beneficial effects on host energy metabolism of shot-chain fatty acids and vitamins produced by commensal and probiotic bacteria," Microbial Cell Factories 16:79: 1-10 (2017).
Intermountain Healthcare. 2015. Irritable Bowel Syndrome (IBS). Retrieved from: https://intermountainhealthcare.org/services/gastroenterology/conditions/irritable-bowel-syndrome/.2015. 3 pages.
Lombardo L; et al "New insights into Lactobacillus and functional intestinal disorders", Minerva Gastroenterologica E Dietologica, Edizioni Minerva Medica, Torino, IT, vol. 54, No. 3. 2008.
Lombardo, Lucio et al., "Clinical Evaluation of *Lactobacillus paracasei* Subsp. Paracasei F19 with Gluco-Oligosaccharides in the Short-term Treatment of Irritable Bowel Syndrome" Microbial Ecology in Health and Disease 21: 28-32 (2009).
Martin R. et al. "Role of commensal and probiotic bacteria in human health: a focus on inflammatory bowel disease", Microbial Cell Factories2013, 12: 71.
Matthes H. et al. Clinical trial: probiotic treatment of acute distal ulcerative colitis with rectally administered *Escherichia coli* Nissle I 917 (EcN), BMC Complementaty and Alternative Medicine2010, 10: 13.
Mazzuoli S. et al. "Definition and evaluation of mucosal healing in clinical practice", Digestive and Liver Disease2013, 45, 969-977.
Michail et al., "Gut Microbiota is Not Modified by Randmized, Double-Blind, Placebo-Controlled Trial of VSL #3 in Diarrhea-Predominant Irritable Bowel Syndrome". (Probiotics & Antimicro Prot. (2011) 3: 1-7).
Milani et al., Assessing the fecal microbiota: and optimized ion torrent 16S rRNA gene-based analysis protocol. PLoS One. 2013; 8(7); e68739, 12 pages. Published2013.
Montalto M. et al., "Clinical trial: the effects of a probiotic mixture on non-steroidal anti-inflammatory drug enteropathy—a randomized, double-blind, cross-over, placebo-controlled study"*Aliment Pharmacol Ther*,2010, pp. 209-214, 6 pages.
Muyzer et al., "Profiling of Complex Microbial Populations by Denaturing Gradient Gel Electrophoresis Analysis of Polymerase Chain Reaction-Amplified Genes Coding for 16S rRNA," Applied and Environmental Microbiology 59:595-700(1993).
Necas J. et al. "Hyaluronic acid (hyaluronan): a review", Veterinarni Medicina, 2008, 53(8): 397-411.
Neiwert et al., "Structural Investigation of rhamnose-rich polysaccharides from *Streptococcus dysgalactiae* bovine mastitis isolate" Carbohydrate Research, vol. 389,2014. pp. 192-195.
Non-Final Office Action for U.S. Appl. No. 16/308,330, filed Dec. 7, 2018 on behalf of Sofar S.P.A..dated May 14, 2020. 23 Pages.
Non-Final Office Action for U.S. Appl. No. 14/916,961, filed Mar. 4, 2016 on behalf of Sofar S.P.A.dated Jun. 30, 2017. 21 pages.
Non-Final Office Action for U.S. Appl. No. 14/916,961, filed Mar. 4, 2016 on behalf of Sofar S.P.A.dated Jul. 25, 2019. 18 pages.

Non-Final Office Action for U.S. Appl. No. 15/305,470, filed Oct. 20, 2016 on behalf of Sofar SPA.dated Aug. 22, 2019. 8 pages.
Non-Final Office Action for U.S. Appl. Bo. 14/916,959, filed Mar. 4, 2016 on behalf of Sofar S.P.A.dated Mar. 13, 2020 25 pages.
Non-Final Office Action for U.S. Appl. No. 14/916,959, filed Mar. 4, 2016 on behalf of Sofar SPA.dated Aug. 31, 2017. 27 pages.
Non-Final Office Action for U.S. Appl. No. 14/916,959, filed Mar. 4, 2016 on behalf of Sofar SPA. dated Nov. 19, 2018. 15 pages.
Non-Final Office Action for U.S. Appl. No. 15/305,470, filed Oct. 20, 2016 on behalf of Sofar SPA.dated Mar. 26, 2018. 10 pages.
Office Action in corresponding Chinese Patent Application No. 201480049296.4, dated Aug. 27, 2019.
Office Action in Corresponding Japanese Patent Application No. 2016-564193, datedApr. 2, 2019.
Okuda et al., "Virtual metagenome reconstruction from 16S rRNA gene sequences".*Nature Communications*,2012. 8 pages.
Oliva S. et al. "Randomised clinical trial: the effectiveness of Lactobacillus Reuteri ATCC 55730 rectal enema in children with active distal ulcerative colitis", Aliment. Pharmacol. Ther.2012, 35: 327-334.
Olveira et al; "Lactobacillus paracasei Reduces Intestinal Inflammation in Adoptive Transfer Mouse Model of Experimental Colitis", Clinical and Developmenta Immunology, vol. 23, No. 5, Jan. 1, 2011, pp. 1077-13.
Orlando A. et al. "Clinical implications of mucosal healing in the management of patients with inflammatory bowel disease", Digestive and Liver Disease2013, 45, 986-991.
Plant et al., "Association of *Laclobacillus* spp. with Peyer's Patches in Mice", Clinical and Diagnostic Laboratory Immunology 8: 320-324 (2001).
Polak-Berecka et al., "Physiocochemical characterization of exopolysaccharides produced by lactobacillus rhamnosus on various carbon sources", Carbohydrate Polymers, vol. 117, 2015. pp. 501-509.
Price R.D. et al. "Hyaluronic acid: the scientific and clinical evidence", Journal ofPlastic, Reconstructive & Aesthetic Surgery2007, 60: 1110-1119.
Restriction Requirement for U.S. Appl. No. 14/916,961, filed Mar. 4, 2016 on behalf of Sofar S.P.A. dated May 10, 2019. 7 pages.
Sambrook et al.Molecular cloning: A Laboratory Manual. 3rd ed., vols. 1,2 and 3 cold Spring Harbor Laboratory Press,2001, 2100 pp.
Sanlibaba et al., "Exopolysaccharides production by lactic acid bacteria",*Applied Microbiology*, vol. 2,May 20, 2016.
Sasaki M.. et al., "Transglucosidase improves the gut microbiota profile of type 2 diabetes mellitus patients: a randomized double-blind, placebo-controlled study"*BMC Gastroenterology*, 13:81,2013.
Savino et al., "Laclobacillus reuteri DSM 17938 in Infantile Colic: A Randomized, Double-Blind, Placebo-Controlled Trial", Pediatrics 126: e526-e533 (2010).
Scaldaferri F. et al. "Gut microbial flora, prebiotics and probiotics in IBD: their current usage and utility", BioMed Research International2013, 9 pages.
Stew Chien Ng et al., "Effect of probiotic bacteria on the intenstinal microbiota in irritable bowel syndrome" Journal of gastroenterology and hepatology.2013.
Spiller et al., "Randomized double blind placebo-controlled trial of *Saccharomyces cerevisiae* CNCM I-3856 in irritable bowel syndrome: improvement in abdominal pain and bloating in those with predominant constipation" *United European Gastroenterology Journal*. 2016.
Stuknyte M. et al., "Potential immunomodulatory activity of bovine casein hydrolysates produced after digestion with proteinases of lactic acid bacteria" *International Dairy Journal*, 21(2011) pp. 763-769.
Taverniti and Gugliemetti et al., "The immunomodulatory properties of probiotic microorganisms beyond their viability (ghost probiotics: proposal of paraprobiotic concept)" Department of Food Science and Microbiolgy (DiSTAM) 6:261-274(2011).
Turnbaugh et al., "The Effect of Diel on the Human Gut Microbiome: A Metagenomic Analysis in Humanized gnolobiotic Mice," Sci Transl Med: (2009).
Tursi et al., "Balsalazide and/or high-potency probiotic mixture (VSL#3) in maintaining remission after attack of acute, uncomplicated diverticulitis of the colon", International Journal of Colorectal

(56) References Cited

OTHER PUBLICATIONS

Disease; Clinical and Molecular Gastroenterology an Surgery, Sprinfer, Berlin, DE. vol. 22, No. 9,Mar. 28, 2007. pp. 1103-1108.

Tursi et al., "Effect of Lactobacillus casei supplementation on the effectiveness and tolerability of a new second-line 10-day quadruple therapy after failure of a first attempt to cure Helicobacter pylori infection," Med Sci Monit 10: CR662-666 (2004).

Tursi et al., "Mesalazine and/or Lactobacillus Casei in maintaining Long-term Remission of Symptomatic Uncomplicated Diverticular Disease of the Colon" Original Paper. Hepato-Gastroenterology. 2008, 55; 916-920.

Tursi et al., "Mesalazine and/or Lactobacillus casei in preventing recurrence of symptomatic uncomplicated diverticular disease of the colon: A Prospective , randomized, open-label study", Journal of Clinical Gastroenterol, Raven Press Ltd, NY, New York. vol. 40, No. 2, Apr. 1, 2006. pp. 312-316.

Tursi et al., "Randomised clinical trial: mesalazine and/or probiotics in maintaining remission of symptomatic uncomplicated diverticula disease—double-blind, randomized, placebo-controlled study" Alimentary Pharmacology & Therapeutics. vol. 38, No. 7.Oct. 19, 2013. pp. 741-751.

U.S. National Library of Medicine, "Effect of Lactobacillus Casei DG (Enterolactis Plus) in Patient with irritable Bowel Syndrome: a Pilot Study", ClinicalTriaals.gov,Feb. 11, 2015.

U.S. National Library of Medicine Efficacy Evaluation of a Commercial Preparation Containing Lactobacillus Casei DG on the Reduction of the Painful Symptoms Related to the Irritable Bowel Syndrome (IBS).*A Pilot Clinical Study*. Feb. 28, 2014.

Valerio et al., "Effects of Probiotic Lactobacillus paracasei-enriched Artichokes on Constipated Patients", J Clin Gastroenterol,Sep. 10, 2010.

Vernia et al. Dig. Disease Sci. (1988) 33(11): 1353-135 (Year: 1988).

Vinogradov et al., "Structural studies of the rhamnoseirch cell wall polysaccharide of lactobacillus casei BL23" *Carbohydrate Research* vol. 435,Oct. 8, 2016. pp. 156-161.

"Why VSL#3" (Obtained from https://vsl3.com/hcp/vsl-info on Aug. 22, 2017 , 4 pages.

Worthley et al. "A human, double-blind, placebo-controlled, crossover trial of prebiotic, probiotic, and symbiotic supplementation: effects on luminal, inflammatory, epigenetic, and epithelial biomarkers of colorectal cancer" (Am J Clin Nutr 2009; 90; 578-86).

Written Opinion for International Application No. PCT/IB2014/064284 filed on Sep. 5, 2014 on behalf of Sofar SPA.dated Jan. 26, 2015. 7 pages.

Written Opinion for International Application No. PCT/IB2014/064285 filed on Sep. 5, 2014 on behalf of Sofar SPA. dated Jan. 29, 2015. 7 pages.

Written Opinion for International Application No. PCT/IB2017/052850 filed on May 15, 2017 on behalf of Sofar SPA.dated Aug. 17, 2017. 6 pages.

Written Opinion for International Application No. PCT/IB2017/053389 filed on Jun. 8, 2017 on behalf of Sofar SPA.dated Oct. 6, 2017. 7 pages.

Written Opinion for International Application No. PCT/IB2017/057576 filed on Dec. 1, 2017 on behalf of Sofar SPA.dated Feb. 22, 2018. 8 pages.

Written Opinion for International Application No. PCT/IB2017/057980 filed on Dec. 15, 2017 on behalf of Sofar SPA. dated Mar. 19, 2018. 8 pages.

Written Opinion for International Application PCT/IB2015/052938 filed on Apr. 22, 2015 on behalf of Sofar SPA.dated Jul. 31, 2015. 5 pages.

Zhang et al., "Isolated exopolysaccharides from lactobacillus rhamnosus GG alleviated adipogenesis mediated by TLR2 in mice" *Scientific reports*. vol. 6, Oct. 27, 2016.

Zheng, L. et al. "Regulation of colonic epithelial repair in mice by toll-like receptors and hyaluronic acid," Gastroenterology2009: 137 2041-2051.

Aden K. et al., "Metabolic Functions of Gut Microbes Associate with Efficacy of Tumor Necrosis Factor Antagonists in Patients with Inflammatory Bowel Diseases" Gastroenterology, 2019, pp. 1279-1292.

Allegretti J. et al., "Short Chain Fatty Acid Profiles Are Altered by Fecal Microbiota Transplantation for the Treatment of Inflammatory Bowel Disease and Recurrent Clostridioides difficile Infection" *Gastroenterology*,2019, 2 pages.

Australian Examination Report for AU Application No. 2017263294 filed on May 15, 2017 on behalf of Sofar S.P.A. dated Oct. 30, 2020 5 pages.

Banasiewicz T. et al., "Determination of butyric acid dosage based on clinical and experimental studies—a literature review" *Gastroenterology Review*,2020, pp. 119-125.

Borren N. et al., "Alterations in Fecal Microbiomes and Serum Metabolomes of Fatigues Patients With Quiescent Inflammatory Bowel Diseases" *Clinical Gastroenterology and Hepatology*,Mar. 2020, 35 pages.

Canadian Office Action for CA Application No. 2,923,392 filed on Sep. 5, 2014 on behalf of Sofar S.P.A. dated Jun. 1, 2020 4 pages.

Cassard L. et al, "Individual strains of Lactobacillus paracasei differentially inhibit human basophil and mouse mast cell activation," Immunity, Inflammation, and Disease vol. 4, Issue 3., 2016. 11 Pages.

Chassard C. et al., "Functional dysbiosis within the gut microbiota of patients with constipated-irritable bowel syndrome" *Alimentary Pharmacology and Therapeutics*, 2012, pp. 828-838.

Chilean Office Action for CL Application No. 201803193 filed on Sep. 5, 2014 dated Apr. 16, 2020 16 pages (English + Original).

Chinese Decision of Rejection for CN Application No. 201480049296.4 filed on Sep. 5, 2014 on behalf of Sofar S.P.A. dated Dec. 9, 2020 (English + Original) 12 pages.

Chinese Office Action for CN Application No. 201480049288 filed on Sep. 5, 2014 on behalf of Sofar S.P.A. dated Sep. 16, 2020 8 pages (English + Original).

Colombian Office Action for CO Application No. NC2018/0010950 filed on Sep. 5, 2014 on behalf of Sofar S.P.A. dated Jul. 27, 2020 11 pages (Partial English + Original).

Communication pursuant to Article 94(3) EPC for EP Application No. 14790322.3 filed on Sep. 5, 2014 on behalf of Sofar S.P.A. dated Jan. 11, 2021 3 pages.

Compare D. et al., "Lactobacillus casei DG and its postbiotic reduce the inflammatory mucosal response: an ex-vivo organ culture model of post-infectious irritable bowel syndrome" *BMC Gastroenterology*,2017, 8 pages.

Cremon C. et al., "Effect of Lactobacillus paracasei CNCM I-1572 on symptoms, gut microbiota, short chain fatty acids, and immune activation in patients with irritable bowel syndrom: A pilot randomized clinical trial" *UEG Journal*, Sep. 2017, 10 pages.

Cui Y. et al., "Revolution of Chronic Diarrhoea" China Medicine, Science, and Technology Publishing House, 1st edition, Jan. 2013, pp. 19-23 (Original + Partial Google Translation).

Eurasian Notification of Grant for Application No. 201690464/28 filed on Sep. 5, 2014 on behalf of Sofar S.P.A. dated Jun. 9, 2020 2 pages (English + Original).

Final Office Action for U.S. Appl. No. 15/305,470, filed Oct. 20, 2016 on behalf of Sofar S.P.A. dated Jul. 10, 2020 21 pages.

Gargari G. et al., "Fecal Clostridiales distribution and short-chain fatty acids reflect bowel habits in irritable bowel syndrome" Environmental Microbiology, Sep. 2018, 31 pages.

Hustoft T. et al., "Effects of varying dietary content of fermentable short-chain carbohydrates on symptoms, fecal microenvironment, and cytokine profiles in patients with irritable bowel syndrome" Neurogastroenterology & Motility, Sep. 2016, 9 pages.

Irritable Bowel Syndrome—Wikipedia, dated Sep. 16, 2020. 33 pages, https://en.wikipedia.org/wiki/Irritable_bowel_syndrome.

Israeli Office Action for Application No. 244391 filed on Mar. 2, 2016 on behalf of Sofar S.P.A. dated Jun. 24, 2020 4 pages (English + Original).

Israeli Office Action for Application No. 269107 filed on Sep. 3, 2019 on behalf of Sofar S.P.A. dated May 17, 2020 5 pages (English + Original).

(56) References Cited

OTHER PUBLICATIONS

Israeli Office Action for IL Application No. 244391 filed on behalf of Sofar S.P.A. dated Oct. 27, 2020 (English + Original) 4 pages.
Japanese Office Action for JP Application No. 2016564193 filed on Apr. 22, 2015 on behalf of Sofar S.P.A. dated Feb. 18, 2020 11 pages (English + Original).
Kay, RM., et al., "Dietary Fiber," J. of Lipid Research, v. 23, 1982. 221-242, 22 Pages.
Langhorst J. et al., "Distinct patterns of short-chain fatty acids during flare in patients with ulcerative colitis under treatment with mesalamine or a herbal combination of myrrh, chamomile flowers, and coffee charcoal: secondary analysis of a randomized controlled trial" European Journal of Gastroenterology & Hepatology, Feb. 2020, 6 pages.
Magnusson M. et al., "The Anti-inflammatory Immune Regulation Induced by Butyrate is Impaired in Inflamed Intestinal Mucosa from Patients with Ulcerative Colitis" Inflammation, Apr. 2020, 11 pages.
Mcfarland, et al., "Strain-Specificity and Disease- Specificity of Probiotic Efficacy: A Systematic Review and Meta-Analysis," Frontiers in Medicine, May 7, 2018. 14 Pages.
Mexican Office Action for MX Application No. MX/a/2016/002766 filed on Sep. 5, 2014 on behalf of Sofar S.P.A. dated Aug. 13, 2020 10 pages (English + Original).
Non-Final Office Action for U.S. Appl. No. 14/916,961, filed Mar. 4, 2016, on behalf of Sofar S.P.A. dated Jan. 7, 2021. 22 Pages.
Pituch A. et al., "Butyric acid in functional constipation" Przeglad Gastroenterologiczny,2013, 4 pages.
Pozuelo M. et al., "Reduction of butyrate and methane producing microorganisms in patients with Irritable Bowel Syndrome" Nature Scientific Reports,Apr. 2015, 12 pages.
Ralf Jager et al., "Probiotic Administration Increases Amino Acid Absorption from Plant Protein: a Placebo-Controlled, Randomized, Double-Blind, Multicenter, Crossover Study," Probiotics and Antimicrobial Proteins, 2020. 10 Pages.
Restriction Requirement for U.S. Appl. No. 16/465,237, filed May 30, 2019 on behalf of Sofar S.P.A. dated Dec. 21, 2020 8 pages.
Ringel-Kulka T. et al., "Short Chain Fatty Acids and Intestinal Transit in Patients With Irritable Bowel Syndrome and Healthy Controls" AGA Abstracts,May 2012, 1 page.
Scarpellini E. et al., "Efficacy of butyrate in the treatment of diarrhea-predominant irritable bowel syndrome" Digestive and Liver Disease, 2007, 4 pages.
Shi Y. et al., "Function and clinical implications of short-chain fatty acids in patients with mixed refractory constipation" Association of Coloproctology of Great Britain and Ireland, Feb. 2016, 8 pages.
Smokvina T. et al "Lactobacillus paracasei Comparative Genomics: Towards Species Pan-Genome Definition and Exploitation of Diversity," Plos One, Jul. 19, 2013. 16 Pages.
Sun Q. et al., "Alterations in fecal short-chain fatty acids in patients with irritable bowel syndrome" Systematic Review and Meta-Analysis,Jan. 2019, 12 pages.
Third Chinese Office Action for CN Application No. 201480049296.4 filed on Sep. 5, 2014 on behalf of Sofar S.P.A. dated Mar. 18, 2020 13 pages (English + Original).
Turco F. et al., Bacterial stimuli activate nitric oxide colonic mucosal production in diverticular disease. Protective effects of L. casei DG (Lactobacillus paracasei CNCM I-1572) UEG Journal, Nov. 2016, 10 pages.
Turco F. et al., "Enteroglial-derived S100B protein integrates bacteria-induced Toll-like receptor signalling in human enteric glial cells" Gut Neurogastroenterology, vol. 63, Mar. 2014, Originally Published online Jan. 3, 2013, 12 pages.
Tursi A. et al., "Assessment of Fecal Microbiota and Fecal Metabolome in Symptomatic Uncomplicated Diverticular Disease of the Colon" J. Clin Gastroenterol,Oct. 2016, 4 pages.
Tursi A. et al., "Fecal Microbiota, Fecal and Urinary Metabolic Profiling and Symptomatic Uncomplicated Diverticular Disease of the Colon" Digestive and Liver Disease, 2017, 1 page.
Tursi A. et al., "Natural History of Symptomatic Uncomplicated Diverticular Disease: A 13-Year Prospective Study" AGA Abstracts,Apr. 2017, 1 page.
Wang Y. et al., "Emerging Infectious Diseases" Science and Technology Documents Publishing House, 1st edition, Jan. 2006, pp. 310-312 (Original + Partial Google Translation).
Watanabe I. et al., "KT-11" Food Style 21, vol. 17, No. 6, pp. 62-64,2013. 5 pages (Machine Translation + Original).
Zhuang M. et al., "Abundance of probiotics and butyrate-production microbiome manages constipation via short-chain fatty acids production and hormones secretion" Molecular Nutrition & Food Research, Jul. 2019, 41 pages.
Zhuang M. et al., "Systematic Review and Meta-analysis: Short-Chain Fatty Acid Characterization in Patients With Inflammatory Bowel Disease" Inflammatory Bowel Disease,Nov. 2019, 13 pages.
Balzaretti S. et al., "A novel hetero-exopolysaccharide mediates the recognition of Lactobacillus paracasei DG by the immune system" Pharmabiotics Conference2015, Paris, Oct. 29-30, 2015, 1 page.
Bienenstock J et al., "New insights into probiotic mechanisms" Gut Microbes, vol. 4 Issue 2, Apr. 2013, 7 pages.
Brussow H. "Problems with the concept of gut microbiota dysbiosis" Microbial Biotechnology, vol. 13(2), 2020, pp. 423-434.
Canadian Examination Search Report for CA Application No. 2,923,390 filed on Sep. 5, 2014 on behalf of SOFAR S.P.A. dated Jan. 26, 2021 4 pages.
Colombian Office Action for CO Application No. NC2018/0010954 filed on Nov. 1, 2018 on behalf of Sofar S.P.A. Mail dated Feb. 5, 2021 9 pages (Partial English + Original).
Colombian Office Action for CO Application No. NC2019/0007116 filed on Jul. 2, 2019 on behalf of SOFAR S.P.A. dated Jan. 15, 2021 19 pages (English + Original).
Declaration for the self-archiving of the doctoral thesis for "Exploring Lactobacillius Paracasei Probiosis and Metabolic Potential" by Balzaretti, Silvia Dated: Nov. 20, 2015 4 pages (English + Original).
Koebnick C. et al., "Probiotic beverage containing Lactobacillus casei Shirota improves gastrointestinal symptoms in patients with chronic constipation" Can J Gastroenterol, vol. 17 No. 11, Nov. 2003, pp. 655-658.
Laws A. et al., "Determination of the structure and molecular weights of the exopolysaccharide produced by Lactobacillus acidophilus 5e2 when grown on different carbon feeds." Carbohydr Res. Feb. 4, 2008;343(2):301-7.
Mexican Office Action for MX Application No. MX/a/2016/002766 filed on Sep. 5, 2014 onbehalf of SOFAR S.P.A. dated Mar. 18, 2021 10 pages (English + Original).
Non-Final Office Action for U.S. Appl. No. 14/916,959, filed Mar. 4, 2016 on behalf of SOFAR S.P.A. dated Apr. 13, 2021 33 pages.
Paoluzi O.A., et al. "Low efficacy of levofloxacin-doxycycline-based third-line tripletherapy for Helicobacter pylori eradication in Italy." World Journal of Gastroenterology21: 6698-705, Jun. 2015.
Rosania R. et al. "Effect of probiotic or prebiotic supplementation on antibiotic therapy in the small intestinal bacterial overgrowth: a comparative evaluation." Curr Clin Pharmacol. May 2013; 8(2):169-72. 5 pages.
Screenshot from the web-archive of the Milano University, Nov. 23, 2015, 2 pages (English + Original).
Tuohy K.M. et al., "Survivability of a probiotic Lactobacillus casei in the gastrointestinal tract of healthy human volunteers and its impact on the faecal microflora" Journal of Applied Mircrobiology, 2007, pp. 1026-1032.
Canadian Office Action for CA Application No. 2,923,392 filed on Sep. 5, 2014 on behalf of Sofar S.P.A. dated Apr. 1, 2021 4 pages.
Canani R. B. et al., "Potential beneficial effects of butyrate in intestinal and extraintestinal diseases" World Journal of Gastroenterology, vol. 17 no. 12, Mar. 2011, 10 pages.
Chooi E et al., "Chronic atrophic gastritis is a progressive disease: analysis of medical reports from Shanghai (1985-2009)" Singapore Med J, 2012, 53 (5), pp. 318-324.
Colledge H. "Atrophic Gastritis: Causes. Symptoms, & Treatment" Healthline, Sep. 2018, 5 pages.
Colombian Office Action for CO Application No. NC2018/0010950 filed on May 15, 2017 on behalf of SOFAR S.P.A. dated May 3, 2021 9 pages (English + Original).

(56) References Cited

OTHER PUBLICATIONS

De Backer A. I. et al., "Intestinal stenosis from mesenteric injury after blunt abdominal trauma" Eur. Radiol., 1999, pp. 1429-1431.
Gould M. et al., "Diabetic diarrhea" Current Gastroenterology Report, 2009, pp. 354-359 (Abstract only).
Jarbrink-Sehgal M. E. et al., "Symptomatic Diverticulosis is Characterized by Loose Stools" *Clinical Gastroenterology and Hepatology*, 14: 1763-1770, Dec. 2016, 9 pages.
Laval G. et al., "The use of steroids in the management of inoperable intestinal obstruction in terminal cancer patients: do they remove the obstruction?" Palliative Medicine, 2000, pp. 3-10.
Mangili G. et al., "Palliative care for intestinal obstruction in recurrent ovarian cancer: a multivariate analysis" *BMJ Journals*, 2005, 5 pages (Abstract Only).
Miceli E. et al., "Common Features of Patients with Autoimmune Atrophic Gastritis" *Clinical Gastroenterology and Hepatology*, 2012, pp. 812-814.
Non-Final Office Action for U.S. Appl. No. 16/465,237, filed May 30, 2019, on behalf of Sofar S.P.A. dated Jul. 9, 2021. 37 Pages.
Non-Final Office Action for U.S. Appl. No. 16/308,330, filed Dec. 7, 2018 on behalf of SOFAR S.P.A. dated Apr. 30, 2021. 38 Pages .
Notice of Allowance for U.S. Appl. No. 15/305,470, filed Oct. 20, 2016 on behalf of Sofar S.P.A. dated Jun. 1, 2021 15 pages.
Restriction Requirement for U.S. Appl. No. 16/467,797, filed Jun. 7, 2019 on behalf of Sofar S.P.A. dated Jun. 15, 2021 6 pages.
Rodriguez-Castro K. I. et al., "Clinical manifestations of chronic atrophic gastritis" Acta Biomed, vol. 89, 2018, pp. 88-92.
Scarpignato C. et al., "Management of colonic diverticular disease in the third millennium: Highlights from a symposium held during the United European Gastroenterology Week 2017" Therapeutic Advances in Gastroenterology, vol. 11, Mar. 2018, pp. 1-21.
Wells D. "Gastritis Diet: What to Eat and What to Avoid" Healthline, Jul. 2020, 11 pages.
Zhang, Z., et al., "Isolated exopolysaccharides from Lactobacillus rhamnosus GG alleviated adipogenesis mediated by TLR2 in mice," *Sci Rep6*, 36083, Oct. 27, 2016. 13 Pages, https://doi.org/10.1038/srep36083.
Colombian Office Action for Colombian Application No. NC2019/0006257 filed on Dec. 15, 2017 on behalf of SOFAR S.P.A. dated May 13, 2021. 3 pages (English + Original).
Final Office Action for U.S. Appl. No. 16/308,330, filed Dec. 7, 2018, on behalf of SOFAR S.P.A. dated Feb. 9, 2022. 22 Pages.
Patel, R., et a., "New Approaches for Bacteriotherapy: Prebiotics, New-Generation Probiotics, and Synbiotics," *Clinical Infectious Diseases*, vol. 60, Issue supplement 2, May 15, 2015. pp. S108-S121. 15 Pages, https://doi.org/10.1093/cid/civ177.
Allowance of the Brazilian patent application BR 11 2016 005059 2 published in the Official Bulletin n⁰ of Oct. 26, 2021 (Portuguese Only).
Canadian Office Action for CA Application No. 2,923,390 filed on Sep. 5, 2014 on behalf of SOFAR S.P.A. dated Nov. 29, 2021 5 pages.
Chinese Office Action for CN Application No. 201780029401.1 filed on May 15, 2017 on behalf of SOFAR S.P.A. dated Dec. 15, 2021 (English + Original) 24 pages.
Colombian Office Action for CO Application No. NC2018/0010950 filed on May 15, 2017 on behalf of SOFAR S.P.A. dated Oct. 14, 2021 (Partial English + Original) 9 pages.
Colombian Office Action for CO Application No. NC2019/0007116 filed on Jul. 2, 2019 on behalf of SOFAR S.P.A. dated Sep. 29, 2021 12 pages (English + Original).
Corrected Notice of Allowability for U.S. Appl. No. 15/305,470, filed Oct. 20, 2016 on behalf of SOFAR S.P.A. dated Jan. 10, 2022 4 pages.
Final Office Action for U.S. Appl. No. 14/916,959, filed Mar. 4, 2016 on behalf of Sofar S.P.A. dated Dec. 29, 2021. 29 Pages.
Mexican Office Action for MX Application No. MX/a/2016/022766 filed on Sep. 5, 2014 on behalf of SOFAR S.P.A. dated Oct. 26, 2021 (Partial English + Original) 12 pages.

Non-Final Office Action for U.S. Appl. No. 16/467,797, filed Jun. 6, 2019 on behalf of SOFAR S.P.A. dated Dec. 14, 2021 35 pages.
Notice of Allowance for U.S. Appl. No. 15/305,470, filed Oct. 20, 2016, on behalf of SOFAR S.P.A. dated Nov. 3, 2021. 8 Pages.
Salvetti E. et al., "The Genus Lactobacillus: A Taxonomic Update" *Probiotics & Antimicro. Prot.*, Nov. 2012, vol. 4, pp. 217-226.
Yuanning S. et al., "Analysis of Lactic Acid Bacteria Protein Dissolution and Aroma Production Ability" Chinese Brew, vol. 33 no. 3, Dec. 31, 2014 (English Abstract + Original) 4 pages.
Australian Examination Report for AU Application No. 2017367302 filed on Dec. 1, 2017 on behalf of SOFAR S.P.A. dated Jul. 23, 2021 4 pages.
Bacteriotherapy—Merriam-Webster Medical Dictionary, Archive Date: Apr. 26, 2016, 6 pages.
Bassi R. "Mesalazine + Lactobacillus paracasei CNCMI1572 vs Mesalazine alone in preventing recurrence of symptom of diverticular disease: a prospective, randomize, open-label study." *Colorectal Disease*, 2019 1 pages.
Bassi R. "Preventing recurrence of symptomatic diverticular disease of the colon: mesalazine with or without Lactobacillus case DG: a prospective randomized, open label study." European Society of Coloproctology, 2015, 1 page.
Capsule (Pharmacy)—Wikipedia, the free encyclopedia, Archive Date: Apr. 10, 2016, 4 pages.
Chilean Office Action for CL Application No. 201901493 filed on Dec. 1, 2017 on behalf of Sofar S.P.A. dated May 6, 2021 24 pages (English + Original).
Chinese Office Action for CN Application No. 201480049288X filed on Sep. 5, 2014 on behalf of Sofar S.P.A. dated Aug. 12, 2021 (English + Original) 15 pages.
Colombian Office Action for CO Application No. NC2018/0010954 filed on Jun. 2, 2019 on behalf of Sofar S.P.A. dated Jun. 30, 2021 8 pages (Partial English + Original).
Communication pursuant to Article 94(3) EPC for EP Application No. 17817173.2 filed on Dec. 1, 2017 on behalf of SOFAR S.P.A. dated Sep. 29, 2021 6 pages.
Dore J. et al., "The Human Intestinal Microbiota; From Phylogenetics to Functional Metagenomics" *Old Herborn University*, 2010, pp. 15-26.
Dysbiosis—Wikipedia, the free encyclopedia, dated Mar. 31, 2014 https://web.archive.org/web/20140331225522/http://en.wikipedia.org/wiki/Dysbiosis , 4 pages.
Eurasian Office Action for EA Application No. 202090097/28 filed on Sep. 5, 2014 on behalf of Sofar S.P.A. dated Aug. 16, 2021 (English + Original) 10 pages.
Ferrario, et al., "Modulation of Fecal Clostridiales Bacteria and Butyrate by Probiotic Intervention with Lactobacillus paracasei DG Varies among Healthy Adults1-3" J. Nutritional Epidemiology, 144. Sep. 3, 2014. pp. 1787-1796. 10 Pages.
Final Office Action for U.S. Appl. No. 14/916,961, filed Mar. 4, 2016, on behalf of SOFAR S.P.A. dated Oct. 14, 2021. 26 Pages.
Gould, M., et al., "Diabetic Diarrhea," Current Gastroenterology Reports, 11: 354-359. Full paper. 2009. 7 Pages.
Haenel H. "Human Normal and Abnormal Gastrointestinal Flora" American Journal of Clinical Nutrition, vol. 23 no. 11, Nov. 1970, pp. 1433-1439.
Iebba V. et al., "Eubiosis and Dysbiosis: the two sides of the microbiota" New Microbiologica, vol. 39, 2016, pp. 1-12.
John Hopkins Medicine—Fecal Transplantation (Bacteriotherapy), John Hopkins Division of Gastroenterology and Hepatology, Archive Date: Apr. 2016, 2 pages.
Leonel, A.J., et al. "Butyrate: implications for intestinal function," Current Opinion in Clinical Nutrition and Metabolic Care 15(5): 474-479. 2012. 6 Pages.
Notice of Allowance for U.S. Appl. No. 15/305,470, filed Oct. 20, 2016, on behalf of SOFAR S.P.A. dated Sep. 8, 2021. 8 Pages.
Restriction Requirement for U.S. Appl. No. 17/090,669 filed on Nov. 5, 2020, on behalf of SOFAR S.P.A. dated Sep. 3, 2021. 7 Pages.
Tsimmerman Y. S. "Eubiosis and Dysbiosis of Gastrointestinal Tract: Myths and Reality" *Perm State Medical Academy*, 2013, 27 pages.

(56) References Cited

OTHER PUBLICATIONS

World Gastroenterology Organisation Global Guidelines "Probiotics and prebiotics" Feb. 2017, 35 pages.

* cited by examiner

USE OF PROBIOTICS FOR IMPROVING PROTEIN ABSORPTION

CROSS-REFERENCE TO RELATED APPLICATIONS

This application is a 371 National Stage application of International PCT Application No. PCT/IB2017/052850, filed May 15, 2017, and claims priority to Italian Patent Application No. 102016000083376, filed Aug. 8, 2016, and to U.S. Provisional Patent Application No. 62/335,926, filed May 13, 2016, all of which are incorporated herein by reference in their entirety.

TECHNICAL FIELD

The present invention relates to the use of probiotics, preferably one or more probiotic bacteria, to increase the absorption of proteins or the bioavailability thereof, preferably in individuals with increased protein and/or energy requirements, preferably elderly persons, children, pregnant women or athletes.

STATE OF THE ART

Proteins are an essential part of living organisms and are formed by the union of simpler molecules called amino acids that bind together through peptide bonds.

In the human body about 50,000 different protein molecules are present; their function is determined by their amino acid sequence. Through a series of reactions, our body is capable of autonomously synthesising the proteins it needs from the single amino acids contained in foods.

Many proteins belong to the category of enzymes, whose function is to catalyse the biochemical reactions that are vital for the metabolism of organisms.

Some have structural and mechanical functions, like actin and myosin in muscles, collagen in bones and tissues, and as components of the cell cytoskeleton.

Other proteins are important mediators in the transmission of inter- and intracellular signals, in the immune response, in cell adhesion mechanisms and in the cell division cycle.

Since proteins cannot be absorbed as such and transported in the circulation, several enzymes present in the lumen of the gastrointestinal tract intervene in their digestion, breaking them down into single amino acids.

During the digestive process, the majority of proteins are completely reduced into single amino acids.

The digestion of these macromolecules begins in the stomach, where the combined action of pepsinogen and hydrochloric acid leads to the formation of oligopeptides (short amino acids chains of less than ten units).

This digestion is then completed by the intestinal proteases of pancreatic origin (dumped into the duodenum) and produced by the membranes of the intestine itself (situated on the brush border). For this reason, protein digestion is normal even after the surgical removal of the stomach.

The above-mentioned proteases are divided into endoproteases (that hydrolyse the internal peptide bonds of proteins: chemotripsin, elastase, tripsin) and exopeptidases (that hydrolyse the terminal amino acid of the protein: carboxypeptidase, aminopeptidase, dipeptidase).

Protein digestion is completed at the intestinal level, thanks precisely to the action of exopeptidases, present in the microvilli of the small intestine, which lead to the formation of single amino acids, dipeptides and tripeptides, which can thus be absorbed at the site of the mucosa via a $Na^+$ or $H^+$ symport mechanism.

Moreover, intestinal flora present in the small intestine, above all lactobacilli, contribute to further digesting the peptides by acting also on the ones not completely hydrolysed by the proteases themselves. Only a small portion, equal to about 5%, arrives in the colon, where it undergoes as well the action of the resident bacterial flora (lactobacilli and bifidobacteria).

Once absorbed, the single amino acids are transported to the liver by specific carriers and here they can:
  be used as such and intervene in the immune response, in the synthesis of hormones and vitamins, in the transmission of nerve impulses, in the production of energy and as catalysts in many metabolic processes;
  participate in protein synthesis, an inverse process in respect to the digestive one which has the purpose of providing the body with materials for the growth, maintenance and reconstruction of cellular structures;
  if present in excess, be used for energy purposes (gluconeogenesis) or converted into fat deposits.

A small portion of proteins present in foods, however, is not absorbed and is eliminated as such with faeces (5%).

Some peptides made up of more than three amino acids are absorbed by transcytosis and as such they can represent a significant element for the development of allergies and food intolerances.

The human body breaks down proteins daily while synthesising others. This process is defined as protein turnover. In this process, some amino acids are oxidated, and the resulting nitrogen is lost in the form of urea, creatinine and other derived substances. With a normal protein intake, only 4% of the proteins turned over may be lost.

This situation can be determined by the amount of protein that is ingested, i.e. by a high or a low daily protein intake. The nitrogen is mainly dispersed through urine, but a part is also eliminated through sweat, faeces, skin or nails.

The nitrogen balance compares the amount of nitrogen (from dietary proteins) introduced into the body with the nitrogen that is lost. If an individual takes in more nitrogen than he/she loses, he/she is said to have a positive nitrogen balance and deposits nitrogen in the body. If an individual consumes the same amount of nitrogen as he/she loses, he/she is said to be in a situation of nitrogen equilibrium, whereas if an individual loses more nitrogen than he/she consumes, he/she has a negative nitrogen balance and loses body proteins.

Since catabolism or the amino acids breakdown is the principal cause of nitrogen loss, the expulsion of nitrogen is an indicator of the amino acids catabolism.

Protein requirements are defined by the amount of dietary proteins necessary to compensate for and offset the loss of nitrogen on a daily basis, so that a person maintains a nitrogen balance. This is determined by measuring the excretion of nitrogen when the person follows a protein-free diet. Since the intake of dietary nitrogen is equal to zero, all of the nitrogen expelled originates from the breakdown and catabolism of body proteins. As mentioned, this value presumes the presence of sufficient food calories and a normal proportion of food carbohydrates.

When we refer to a normal healthy body, we exclude situations in which the nitrogen balance can be altered, such as pregnancy, breastfeeding, old age, sports activity, convalescence, growth (children, adolescents), or the aftermath of a low-calorie diet or anorexia.

Protein requirements are the amount of proteins our body needs to satisfy its energy needs and maintain good health.

These amounts vary according to several factors, such as: age, gender, state of health, work activity or sports activity.

The average protein requirements of a person are inversely proportional to age. For example: about 2 g/kg/day in newborns, about 1.5 g/kg/day at 5 years, and about 1.2 g/kg/day in adolescence-adulthood.

A protein is digestible if a high proportion of its amino acids reach the body's cells so that they can synthesise the proteins they need.

Not all sources, however, are used equally well by the body and the bioavailability of proteins themselves varies according to the protein source. In fact, nearly 100% of animal proteins undergo intestinal absorption, whereas vegetable proteins show a much lower absorption: 52% for lentils, 70% for chick peas and 36% for wheat.

In order to increase protein bioavailability, the body breaks down the large amounts of protein molecules into their simpler units, amino acids.

In adults, a protein deficiency causes a loss of vigour and strength, mental depression, profound weakness, poor resistance to infections, delayed scarring of wounds and slow recovery from illnesses. Even hair and nails are affected, and this problem is more serious for children.

As pointed out, in order for the body to be able to use proteins, they must be broken down into free amino acids or peptides. The proteins in natural yogurt containing live lactobacilli arrive at the digestion process in already pretreated conditions. Indeed, even before it is eaten, the bacteria present have begun to transform the proteins, fats and sugars of the milk into easily digestible components. As a result, the nutrients in natural yogurt are immediately available and ready for use by our body.

The fermentation process measurably increases the protein content of fermented foods. Even protein-rich foods like milk contain more proteins after fermentation than before the bacteria interacted with them. When we eat a fermented food like yogurt, not only do we have the advantages of the added proteins, but this food in a partially pre-digested, completely bioavailable form is also very appreciated by the body.

Object of the Invention

With the aim of satisfying, in general, the average daily protein requirements and particularly in conditions in which the nitrogen balance is altered, the present invention proposes using one or more probiotics in order to increase protein bioavailability in the body or in any case the absorption (assimilation) thereof, preferably at the intestinal site.

DETAILED DESCRIPTION OF PREFERRED EMBODIMENTS OF THE INVENTION

A first aspect of the present invention relates to the use of probiotics for increasing the absorption and/or the bioavailability of proteins and/or of protein derivatives in an individual.

Preferably, the individual has a need for an increased protein absorption/bioavailability, for example as in the case of elderly persons, children, pregnant women or athletes. In other words, said probiotics can be taken in order to increase the protein and/or energy intake every time the need arises for an individual.

In this context "probiotic" means, according to what has been established by the FAO and WHO: "Live microorganisms which, when administered in adequate amounts, confer a health benefit on the host".

In other words, probiotics are microorganisms which demonstrate to be able, once ingested in adequate amounts, to perform functions that are beneficial for the body, substantially echoing the definition of the two above-mentioned organisations.

In the context of the present invention, protein requirements means the amount of proteins our body needs to satisfy its energy needs and maintain good health.

These amounts vary according to several factors, such as: age, gender, state of health, work activity or sports activity.

The average protein requirements of a person are inversely proportional to age. For example: about 2 g/kg/day in newborns, about 1.5 g/kg/day at 5 years, and about 1.2 g/kg/day in adolescence-adulthood Preferably, the proteins to which reference is particularly made in the context of the present invention are selected from among animal and vegetable proteins, including: egg white, milk serum proteins, preferably WPI 90% and WPC 80%; lupin proteins, preferably protilup 450; soy proteins; pea proteins and caseinate protein, preferably calcium caseinate protein and rice proteins.

In fact, the applicant has surprisingly found that following the administration of probiotics, in particular of bacteria of the genus *Lactobacillus*, preferably the strains L. casei DG® (*Lactobacillus paracasei* CNCM I-1572) and/or *Lactobacillus paracasei* LPC-S01, one observes a 10-20% increase in the protein/energy absorption/bioavailability in the individual who has taken them. In particular, the effect has been observed for caseinate and/or milk serum proteins.

According to a preferred embodiment of the present invention, the probiotics are bacteria and/or yeast and/or other microorganisms, taken individually or in combination.

The bacteria that are particularly preferred for the purposes of the present invention belong to a genus selected from among: *Lactobacillus, Bifidobacterium, Bacillus, Propionibacterium, Streptococcus, Lactococcus, Aerococcus, Enterococcus* and combinations thereof.

More preferably, the bacteria belong to the genus *Lactobacillus* and/or *Bifidobacterium*.

In particular, the *Lactobacillus* is selected from among: *Lactobacillus paracasei, Lactobacillus acidophilus, Lactobacillus amylolyticus, Lactobacillus amylovorus, Lactobacillus alimentarius, Lactobacillus aviaries, Lactobacillus brevis, Lactobacillus buchneri, Lactobacillus casei, Lactobacillus cellobiosus, Lactobacillus coryniformis, Lactobacillus crispatus, Lactobacillus curvatus, Lactobacillus delbrueckii, Lactobacillus farciminis, Lactobacillus fermentum, Lactobacillus gallinarum, Lactobacillus gasseri, Lactobacillus helveticus, Lactobacillus hilgardii, Lactobacillus johnsonii, Lactobacillus kefiranofaciens, Lactobacillus kefiri, Lactobacillus mucosae, Lactobacillus panis, Lactobacillus collinoides, Lactobacillus paraplantarum, Lactobacillus pentosus, Lactobacillus plantarum, Lactobacillus pontis, Lactobacillus reuteri, Lactobacillus rhamnosus, Lactobacillus sakei, Lactobacillus salivarius, Lactobacillus sanfranciscensis* and combinations thereof.

More preferably, the lactobacilli are of the species *Lactobacillus acidophilus, rhamnosus* or *paracasei*. Even more preferably, the strains L. casei DG® (*Lactobacillus paracasei* CNCM I-1572) and/or *Lactobacillus paracasei* LPC-S01 (deposited by SOFAR S.p.A. with the German Collection of Microorganisms of the institute DSMZ of Leibniz on Jan. 1, 2016, with deposit number DSM 26760) are used. They can be administered individually or in various combinations.

The bacterial strain L. casei DG® was deposited by SOFAR S.p.A. with the National Collection of Microorganism Cultures of the Pasteur Institute of Paris on Jun. 5, 1995, with deposit number CNCM I-1572. Initially, the strain had the designation *Lactobacillus casei* DG sub. *casei*.

Clearly, use can also be made of other bacteria that are capable of stably colonising the intestine, taking away space from pathogenic bacteria.

The amount of microorganism administered, in particular for the bacteria, is the minimum sufficient to obtain a temporary colonisation of the intestine, preferably at least $10^9$ units of microorganism, bacterium, per day.

The microorganisms, preferably the bacteria, can be administered live and therefore the composition is also definable as a probiotic. Alternatively, the microorganisms that can be used are dead or tyndallized.

In a further embodiment, the microorganisms are in the form of a lysate or extract and therefore the composition is also definable as a paraprobiotic, or a single component, or several components thereof, present at the level of the bacterial wall.

In a further embodiment of the invention, the composition further comprises the metabolic bioproducts generated by the microorganisms defined as postbiotics, and/or any other product of bacterial derivation. Therefore, the composition of the present invention is also a known or presumed probiotic or paraprobiotic or postbiotic or a component of the bacterial wall.

In general, the microorganisms comprised in the composition of the present invention are single microorganisms or combinations of any microbial species specified in the QPS list of the EFSA.

In one embodiment of the present invention, the probiotics can be administered orally, for example in solid form, preferably as pills, capsules, tablets, granular powder, hard-shelled capsules, orally dissolving granules, sachets, lozenges or drinkable vials.

Alternatively, in liquid form, for example as a syrup or beverage, or else they are added to food, for example to yogurt, cheese or fruit juice.

Alternatively, they are formulated in a form capable of exerting a topical action, for example via enema or as a cream.

They can also be administered in combination with amino acids, supplements, vitamins, trace elements such as zinc and selenium, enzymes and/or prebiotic substances, such as fructooligosaccharides (FOS), galactooligosaccharides (GOS), inulin, guar gum or combinations thereof.

The Applicant has found that probiotics in general, and in particular bacteria of the genus *Lactobacillus* and/or *Bifidobacterium*, are very effective in splitting proteins into different peptides compared to what occurs by virtue of the action of digestive enzymes alone. They also act upon molecules that are not completely hydrolysed by human proteases, but whose hydrolysis could be completed by microbial intervention.

The peptides generated by virtue of their action, individual or combined, are more easily absorbed by the body than the starting protein. The final result that is obtained by the action of the probiotics is an increased/improved absorption or, in any case, a greater bioavailability of the proteins to an individual who needs them.

EXAMPLE I

In particular, an in vitro study was set up for the purpose of evaluating the role of probiotic bacteria in protein absorption; in particular, the proteins used by athletes were tested.

The probiotic bacteria used specifically by way of illustrative example are:

L. casei DG® (*Lactobacillus paracasei* CNCM 11572); and
*Lactobacillus paracasei* LPC-S01.

The bacteria were used individually or in combination.

The individual or combined action was verified on various protein substrates. In particular on:
Egg white
Milk serum proteins, WPI 90% and WPC 80%
Lupin proteins, Protilup 450
Soy proteins
Pea proteins
Calcium caseinate
Rice proteins As an indirect assay for evaluating the action of a protease, the overall proteolysis was evaluated by measuring absorbance at 280 nm.

This procedure is based on the quantification of soluble peptides after treatment with TCA so as to determine absorbance at 280 nm, with respect to aromatic amino acids (Phe, Tyr, Trp). Obviously, this method gives a relative indication, as it is based on the assumption that there is an average distribution of peptides containing these residues. It shall be noted that there is a direct proportionality between absorbance values and the concentration of the solution considered. Therefore, in this case high absorbance values indicate high concentrations of the peptides that are generated due to the action of the proteases and of the tested strains. However, this technique has a limit in that very small peptides are not detected and therefore the effect can actually be underestimated.

By way of example, in Table I we present the results obtained with milk serum proteins WPI. They show differences of about 10-20%.

TABLE I

| Treatment | WPI |
|---|---|
| Pepsin | 0.80 ± 0.048 |
| pepsin + pan | 2.29 ± 0.180 |
| pep + pan + SO1 | 2.81 ± 0.191 |
| pep + pan + DG | 2.45 ± 0.192 |
| Complete mix | 2.51 ± 0.141 |

Furthermore, the TCA-soluble peptides generated by the proteolytic action on caseinate with and without probiotics were also quantified.

Specifically, the peptides which showed to be soluble after treatment with TCA were separated by RP-HPLC.

The results obtained from the chromatographic separations—expressed in terms of the total area subtended by the chromatogram with 220 nm detection—are presented in Table II below.

TABLE II

| | Caseinate Substrate | |
|---|---|---|
| Proteolysis conditions | Area (*$10^6$) | Δ |
| pep + pan | 303 | |
| pep + pan + SO1 | 322 | +6% |
| pep + pan + DG | 329 | +9% |

The values shown were calculated from the HPLC plots. In particular, the total area subtended by the peaks related to the peptides produced during the hydrolysis tests under the different conditions used in the assay is shown and the percentage variations relative to the treatment with pepsin and pancreatin (but without microorganisms) are indicated for the various samples.

The results show an increase in proteolysis in the presence of both microorganisms.

As said previously, the proteolytic activity measured in this manner could however be underestimated due to the production of very small protein fragments that do not adhere to the column matrix and are thus lost in the fraction eluted prior to the application of the chromatographic gradient and which are consequently not quantifiable. Or else it could also occur that the use of probiotics increases the proteolytic action in such a way as to fragment the proteins into peptides that are so small as to be immediately eluted from the column.

EXAMPLE II

The proteolysis tests were conducted using the strain *L casei* SO1 or DG individually.

The substrates used were:
milk serum proteins, WPI 90%, batch R2522, supplied by SOFAR
isolated rice proteins supplied by SOFAR,
concentrated serum proteins, WPC 80%, supplied by SOFAR
pea proteins, batch 20150430, supplied by SOFAR Evaluation of Total Proteolysis by Measuring Absorbance at 280 nm The conditions of proteolytic activity are the same as used in the preceding experimental tests.

By way of example we show the results obtained in Table III.

TABLE III

| Treatment | WPI | WPC | Rice |
|---|---|---|---|
| pep + pan | 2.45 | 2.11 | 2.06 |
| pep + pan + SO1 | 2.48 | 2.12 | 2.09 |
| pep + pan + DG | 2.44 | 2.09 | 2.07 |
| pep + pan + mix | 2.50 | 2.11 | 2.11 |

Evaluation of Total Proteolysis by RP-HPLC Separation

With this method we wanted to quantify the peptides generated by the proteolytic action. Specifically, the peptides showing to be soluble after treatment with TFA 0.1%—which constitutes the mobile phase used for HPLC separation—were separated by RP-HPLC. Under these conditions, in fact, most of the protein material that is separable and quantifiable by measuring the absorbance at both 220 nm and 280 nm remains soluble. The results obtained from the chromatographic separations—expressed in terms of the total area subtended by the chromatogram with detection at 220 nm or at 280 nm—are presented in Table IV. It should be observed that the quantification at 220 nm allows to observe also the presence of peptides that do not contain the aromatic residues (Phe, Tyr, Trp), which are instead quantified when absorbance is measured at 280 nm.

The values shown were calculated from the HPLC plots. In particular, the total area subtended by the peaks related to the peptides produced during the hydrolysis tests under the different conditions used in the assay is shown, and the percentage variations relative to the treatment with pepsin and pancreatin (but without microorganisms) are indicated for the various samples.

The results presented in Tables IV and V show that the *L. casei* DG and SO1 strains have a comparable proteolytic activity with respect to the serum protein substrate. In the case of rice proteins, on the other hand, it should be noted that only the *L. casei* SO1 strain shows a proteolytic activity. The *L. casei* DG strain, by contrast, is more active with respect to the pea protein substrate.

TABLE IV

| | Substrate | | | | | | | |
|---|---|---|---|---|---|---|---|---|
| | WPI | | WPC | | rice | | pea | |
| Treatment | Area ($*10^6$) | Δ | Area ($*10^6$) | Δ | Area ($*10^6$) | Δ | Area ($*10^6$) | Δ |
| pep + pan | 125 | | 98 | | 78.2 | | 107 | |
| pep + pan + SO1 | 128 | +3% | 101 | +3% | 80.2 | +3% | 107 | — |
| pep + pan + DG | 131 | +5% | 102 | +4% | 78.4 | — | 111 | +4% |
| pep + pan + mix | 129 | +3% | 104 | +6% | 80.6 | +3% | 114 | +7% |

TABLE V

| | Substrate | | | | | | | |
|---|---|---|---|---|---|---|---|---|
| | WPI | | WPC | | rice | | pea | |
| Treatment | Area ($*10^6$) | Δ | Area ($*10^6$) | Δ | Area ($*10^6$) | Δ | Area ($*10^6$) | Δ |
| pep + pan | 4.5 | | 3.6 | | 5.1 | | 11.9 | |
| pep + pan + SO1 | 4.9 | +9% | 3.9 | +8% | 5.4 | +6% | 12.0 | — |
| pep + pan + DG | 4.8 | +7% | 3.8 | +6% | 5.2 | +2% | 12.2 | +3% |
| pep + pan + mix | 4.9 | +9% | 3.9 | +8% | 5.4 | +6% | 12.6 | +6% |

The invention claimed is:

1. A method of using bacterial strains for increasing the absorption and/or the bioavailability of proteins and/or of energy in an individual, comprising
   administering to an individual bacterial strain *Lactobacillus paracasei* DG having a deposit number CNCM I-1572 and bacterial strain *Lactobacillus paracasei* LPC-S01 having a deposit number DSM 26760 DSMZ in an effective amount to increase the absorption and/or the bioavailability of proteins and/or of energy in the individual, the administering performed orally and/or rectally.

2. The method according to claim 1, wherein said bacterial strains are taken daily by said individual in an amount sufficient to allow gut colonization.

3. The method according to claim 1, wherein said individual is selected from the group consisting of: the elderly, children, pregnant women and athletes.

4. The method according to claim 1, wherein the proteins are selected from the group consisting of: egg white, milk serum proteins; lupin proteins; soy proteins; pea proteins; caseinate proteins; and rice proteins.

5. The method according to claim 1, wherein the bacterial strains are administered by the oral route in solid form, as pills, capsules, tablets, granular powder, hard-shelled capsules, soluble granules, sachets or lozenges; or in liquid form, as a syrup or beverage, or added to food.

6. The method according to claim 1, wherein the bacterial strains are formulated to act topically.

7. The method according to claim 1, wherein the bacterial strains are administered in combination with amino acids, supplements, vitamins, zinc and/or selenium, enzymes and/or prebiotic substances, fructooligosaccharides (FOS), galactooligosaccharides (GOS), inulin, guar gum or a combination thereof.

8. The method of claim 2, wherein the gut colonization is achieved at least $10^9$ colony forming units (CFU) of bacteria/day or of bacteria/dose.

9. The method of claim 1, wherein the bacterial strains are administered via enema or as a cream.

\* \* \* \* \*